United States Patent [19]
Oshino et al.

[11] Patent Number: 5,374,418
[45] Date of Patent: * Dec. 20, 1994

[54] COMPOSITION FOR USE IN ORAL CAVITY

[75] Inventors: Kazushi Oshino, Utsunomiya; Atsushi Yamagishi, Ichikai; Ryozo Nakai, Utsunomiya; Yasuteru Eguchi, Akatsuka-Shinmachi; Tetsuji Iwasaki; Yuichi Hioki, both of Wakayama, all of Japan

[73] Assignee: KAO Corporation, Tokyo, Japan

[*] Notice: The portion of the term of this patent subsequent to Dec. 6, 2011 has been disclaimed.

[21] Appl. No.: 16,234

[22] Filed: Feb. 11, 1993

[30] Foreign Application Priority Data

Feb. 13, 1992 [JP] Japan .................. 4-026746
May 19, 1992 [JP] Japan .................. 4-125998

[51] Int. Cl.$^5$ .................. A61K 7/16; A61K 7/22
[52] U.S. Cl. .................. 424/54; 424/49; 424/57
[58] Field of Search ............. 424/49-88; 427/56, 57

[56] References Cited

U.S. PATENT DOCUMENTS

| | | | |
|---|---|---|---|
| 3,864,472 | 2/1975 | Pensak et al. | 424/54 |
| 4,036,950 | 7/1977 | Baines et al. | 424/54 |
| 4,064,138 | 12/1977 | Saari et al. | 548/344 |
| 4,152,421 | 5/1979 | Tsutsumi et al. | 424/57 |
| 4,256,731 | 3/1981 | Curtis et al. | 424/54 |
| 4,391,798 | 7/1983 | Tavss et al. | 424/52 |
| 4,536,519 | 8/1985 | Suzuki et al. | 514/785 |
| 4,670,575 | 6/1987 | Kurosaki et al. | 558/146 |
| 4,776,976 | 10/1988 | Nakamura et al. | 252/312 |
| 4,820,507 | 4/1989 | Klueppel et al. | 424/54 |
| 4,868,163 | 9/1989 | Takei et al. | 524/76 |
| 4,997,672 | 3/1991 | DeSimone et al. | 426/649 |
| 5,019,373 | 5/1991 | Carter et al. | 424/52 |
| 5,035,881 | 7/1991 | Mori et al. | 424/54 |
| 5,064,640 | 11/1991 | Kieber et al. | 424/52 |
| 5,085,854 | 2/1992 | Fukuda et al. | 424/63 |
| 5,128,122 | 7/1992 | Cerami et al. | 424/49 |

OTHER PUBLICATIONS

Moncrieff "The Chemical Senses" (1944) pp. 388 102 107 237 238 247 266 271 273 275.
Inglett "Symposium Sweeteners" (1974) pp. 235 30 135 138.
Bender "Amino Acid Metabolism" (1975) pp. 203-208.
Zapsalis "Food Chemistry and Nutritional Biochemistry" (1985) pp. 581-591.

*Primary Examiner*—Shep K. Rose
*Attorney, Agent, or Firm*—Oblon, Spivak, McClelland, Maier, & Neustadt

[57] ABSTRACT

A composition for use in the oral cavity is disclosed. The composition comprises (A) an antibacterial compound represented by the following general formula (1), $$A^{m+} \cdot X_m^- \qquad (1)$$

wherein $A^{m+}$ is a nitrogen-containing antibacterial cation and the counter anion $X^-$ represents a monoalkyl phosphate ion, a monoalkenyl phosphate ion, a monoalkyl phosphonate ion, or a monoalkenyl phosphonate ion having a linear or branched alkyl or alkenyl group with 8 to 20 carbon atoms, and m is a valence of the cation A, and (B) a vehicle for use in the oral cavity. It exhibits a remarkablely rapid and continued disinfection effect action against oral cavity bacteria, while providing a good taste. Its disinfection effect is not reduced in the presence of surfactants. In addition, it does not color the tooth.

5 Claims, 2 Drawing Sheets

COMPOSITION FOR USE IN ORAL CAVITY

BACKGROUND OF THE INVENTION

1. Field of the Invention

The present invention relates to a composition for use in the oral cavity, which can disinfect bacteria in the oral cavity, has a reduced bitter or astringent taste, and is useful for the prevention or treatment of oral diseases such as dental caries, periodontosis, and the like.

2. Description of Background Art

Dental caries and periodontosis (e.g., gingivitis, periodontitis), which are typical diseases in the oral cavity are a type of bacterial infection. Dental caries is considered to be caused by *Streptococcus mutans*, gingivitis by *Actinomyces viscosus*, and periodontitis by *Prophyromonas gingivilis, Capnocytophaga ochracea*, and the like.

Accordingly, compositions for oral cavity comprising an antibacterial agent for these bacteria had been developed for the prevention of dental caries and periodontosis, which are commercially available. Examples of such compositions include dentifrices, mouthwashes, and the like, in which a cationic antibacterial compound (e.g., chlorhexidine hydrochloride, cetylpyridinium chloride), a nonionic antibacterial compound (e.g., triclosan), or the like, is incorporated.

However, many of the conventional cationic antibacterial agents give a bitter and astringent taste when incorporated in an amount effective for the disinfection. For example, Yamazaki, et al reports that a gargle comprising 0.04% by weight of benzalkonium chloride is not suitable for common use, since it provides an extremely bitter and astringent taste, even though its effect is remarkable ["Oral cavity disinfection effect of benzalkonium chloride", Journal of Dental Critics, 554, 227 (1988)]. Furthermore, these cationic antibacterial compounds decrease their disinfection effects in the presence of an anionic surfactant in a mouthwash composition. Therefore, their use in combination with a nonionic surfactant was proposed (e.g., Japanese Patent Laid-open (kokai) Nos. 101417/1984, 101418/1984, 282317/1990, 109315/1991). The proposed compositions, however, not only failed to improve the taste, but also provided insufficient disinfection effects due to the poor immediate antibacterial effect exhibited by conventional nonionic antibacterial compounds. Thus, the compositions had a drawback in that they could not exhibit sufficient antibacterial actions during use.

UK Patent No. 1,431,932 discloses a composition for use in the oral cavity for suppressing formation of dental calculus and dental stone, comprising an antibacterial compound which consists of 2 mols of a quaternary ammonium compound and 1 mol of a monoalkyl phosphate. This composition for use in the oral cavity, however, exhibits no prolonged antibacterial effect and does not provide an improved taste. On the other hand, as compositions for use in the oral cavity to Which a phosphate type surfactant is added, Japanese Patent Laid-open (kokai) No. 47542/1978 (U.S. Pat. No. 4,152,421) discloses a dentifrice comprising a monoalkyl phosphate as a foaming agent, which the inventors claim does not change taste of foods and beverages; Japanese Patent Publication (kokoku) No. 500061/1979 (U.S. Pat. No. 4,366,146) proposes a dentifrice for preventing formation of spots comprising a monoalkyl phosphate as a film forming material; and U.S. Pat. No. 4,036,950 discloses a composition for use in the oral cavity having a pH of above 6 and comprising an abrasive, a cationic antibacterial compound, and a polyoxyethylene-alkylether phosphate. Of these publications, Japanese Patent Laid-open (kokai) No. 47542/1978 and Japanese Patent Publication (kokoku) No. 500061/1979 does not mention the combined use of a cationic surfactant and a phosphate, and the composition proposed in U.S. Pat. No. 4,036,950 provides only insufficient improvement in its taste.

Japanese Patent Laid-open (kokai) No. 218605/1990 describes a composition comprising a quaternary ammonium compound and a salt of phosphoric ester and effective as an antibacterial and antiseptic agent for use in the skin or the hair. The specification, however, does not suggest at all the possibility of applying the proposed composition to the oral cavity.

An object of the present invention is to provide a composition for use in the oral cavity which exhibits an immediate and long-continued antibacterial activity to bacteria in the oral cavity, provides a good taste, and does not reduce its antibacterial activity even when a surfactant as a detergent is added.

The inventors of the present invention have undertaken painstaking investigations and found that a composition comprising a specific antibacterial compound and a vehicle for use in the oral cavity provides little bitter or astringent taste, has an excellent antibacterial activity, and exhibits an immediate and long-lasting continued antibacterial effect, even if a surfactant is added. This finding has led to the completion of the present invention.

SUMMARY OF THE INVENTION

Specifically, the above object is achieved in the present invention by the provision of a composition for use in the oral cavity comprising:

(A) an antibacterial compound represented by the following general formula(1 ),

$$A^{m+} \cdot X_m^{-} \qquad (1)$$

wherein $A^{m+}$ is a nitrogen-containing antibacterial cation and the counter anion $X^{-}$ represents a monoalkyl phosphate ion, a monoalkenyl phosphate ion, a monoalkyl phosphonate ion, or a monoalkenyl phosphonate ion having a linear or branched alkyl or alkenyl group with 8 to 20 carbon atoms, and m is a valence of the cation A, and (B) a vehicle for use in the oral cavity.

The above object is further achieved in the present invention by the provision of a composition for use in the oral cavity comprising, in addition to said components (A) and (B), (C) a surfactant represented by the following general formula (7),

$$R^{10}O-\overset{O}{\underset{OZ^2}{\overset{\|}{P}}}-OZ^1 \qquad (7)$$

wherein $R^{10}$ is a linear or branched alkyl or alkenyl group with 8 to 30 carbon atoms, and $Z^1$ and $Z^2$ may be the same or different and each individually represents a hydrogen atom, an alkali metal, an alkyl ammonium group, an alkyl ammonium group with a substituted hydroxy group, or a basic amino acid group residue.

The above object is still further achieved in the present invention by the provision of a composition for use in the oral cavity comprising, (A') an antibacterial compound represented by the following general formula (8), $$A^{m+} \cdot Y_m^{-} \qquad (8)$$

wherein $A^{m+}$ is a nitrogen-containing antibacterial cation and the counter anion $Y^-$ represents a halogen ion or a gluconate ion, and m is a valence of the cation A, and said components (B) and (C), and wherein the molar amount of component (C) is m times or more of that of component (A'). Other objects, features and advantages of the invention will hereinafter become more readily apparent from the following description.

Figure 1:
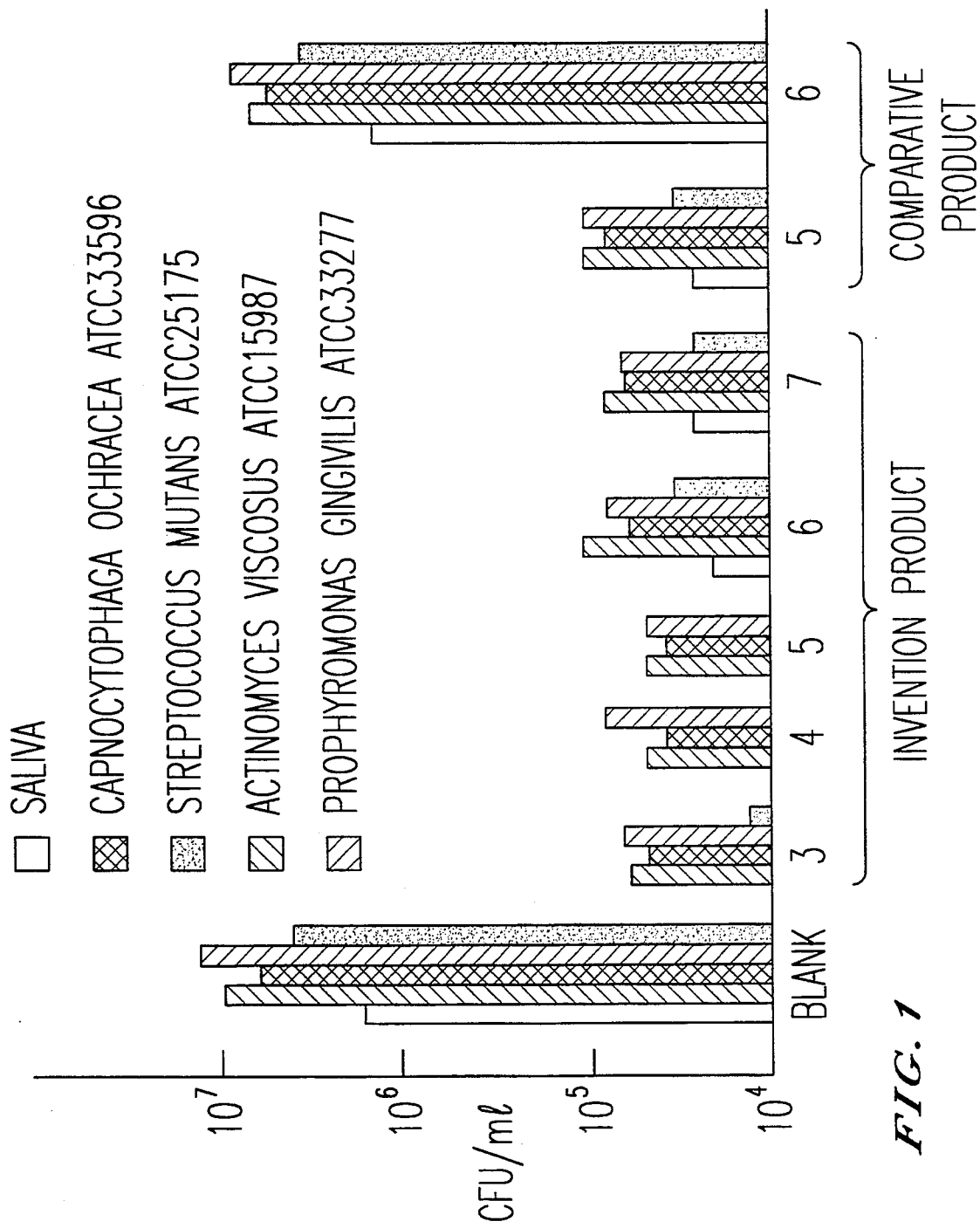
FIG. 1 is a chart showing the results of the disinfection test of the composition in Example 2.

(wherein n is an integer of 1 to 15),

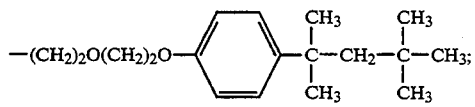

$R^4$ represents a group —$CH_3$, —$CH_2CH_3$, or —$CH_2CH_2OH$; and the counter anion $X^-$ represents a monoalkyl phosphate ion, a monoalkenyl phosphate ion, a monoalkyl phosphonate ion, or monoalkenyl phosphonate ion having a linear or branched alkyl or alkenyl group with 8 to 20 carbon atoms.

Among compounds of general formula (2), those having a linear or branched alkyl group with 8 to 14 carbon atoms, e.g., 2-ethylhexyl group, decyl group, dodecyl group, or tetradecyl group or benzyl group, for at least one of $R^1$ and $R^2$, and methyl group and/or group for others are preferable.

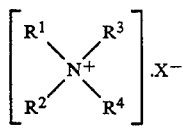  (3)

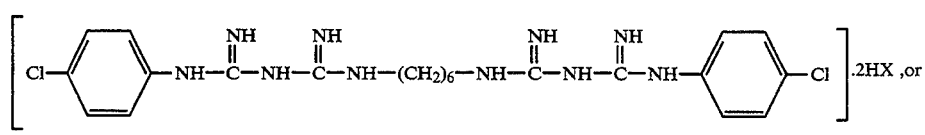  (4)

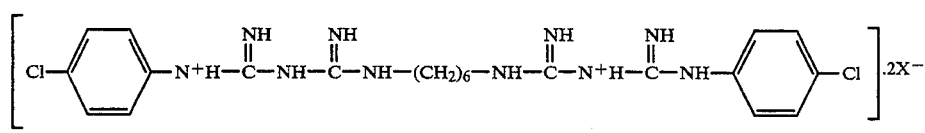  (4')

DETAILED DESCRIPTION OF THE INVENTION AND PREFERRED EMBODIMENTS

Given as examples of antibacterial compounds of said component (A) used in the composition for use in the oral cavity of the present invention are the compounds represented by the following formulas (2) to (4),

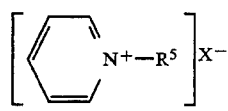  (2)

wherein at least one of $R^1$, $R^2$, or $R^3$ is a linear or branched alkyl or alkenyl group with 8 to 30 carbon atoms, and others are individually a group selected from methyl group, ethyl group, benzyl group, and a group represented by one of the following formulas,

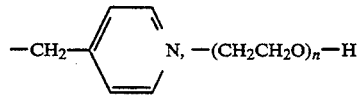

wherein $R^5$ is a linear or branched alkyl group with 10 to 20 carbon atoms, X and $X^-$ may be the same or different and each individually represents a monoalkyl phosphate ion, a monoalkenyl phosphate ion, a monoalkyl phosphonate ion, or a monoalkenyl phosphonate ion having a linear or branched alkyl or alkenyl group with 8 to 20 carbon atoms.

Examples of linear or branched alkyl groups with 10 to 20 carbon atoms represented by $R^5$ in general formula (3) include decyl group, dodecyl group, tetradecyl group, hexadecyl group, octadecyl group, eicosyl group, and the like.

Given as examples of the monoalkyl phosphate ion, monoalkenyl phosphate ion, monoalkyl phosphonate ion, or monoalkenyl phosphonate ion, which are the counter anions represented by $X^-$ or X in formulas (1) to (4), are anions of the following formula (5) or (6),

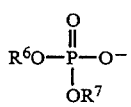  (5)

wherein $R^6$ is a linear or branched alkyl or alkenyl group with 8 to 20 carbon atoms and $R^7$ is a hydrogen atom, an alkali metal, an alkyl ammonium group, an alkyl ammonium group with a substituted hydroxy group, or a basic amino acid group residue; and

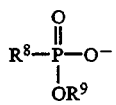 (6)

wherein $R^8$ is a linear or branched alkyl or alkenyl group with 8 to 20 carbon atoms and $R^9$ is a hydrogen atom, an alkali metal, an alkyl ammonium group, an alkyl ammonium group with a substituted hydroxy group, or a basic amino acid group residue.

As $R^6$ and $R^8$ in the above general formula (5) or (6), an alkyl group with 10 to 20 carbon atoms is preferable, 12 to 16 carbon atoms more preferable, and 14 carbon atoms most preferable. Specific examples of such alkyl groups are lauryl, myristyl, and cetyl groups, and the like. $R^7$ and $R^9$ are normally hydrogen atoms. Some portion of counter anions may have an alkali metal (e.g., potassium, sodium), an alkyl ammonium group, an alkyl ammonium group with a substituted hydroxy group, or a basic amino acid group residue for $R^7$ or $R^9$.

The amount of the component (A) in the composition for use in the oral cavity of the present invention is 0.001 to 0% by weight (hereinafter % refers to % by weight), and preferably 0.01 to 1%. An amount outside the above range is not desirable, since if it is less than 0.001%, the antibacterial strength is weakened; if greater than 20%, the stability of the formulation is poor.

Commonly used vehicles for the oral cavity, such as those used in toothpaste, toothpowder, liquid dentifrice, mouthwash, gargle, mouth rinse, gum massage cream, troches, chewing gum, candies, or the like, can be used as vehicles for component (B) in the composition for use in the oral cavity of the present invention.

Such vehicles for the oral cavity which can be used in the composition of the present invention include abrasives, thickening agents, moisturizers, surfactants, perfumes, sweeteners, preservatives, colorants, water, water-soluble fluorine-containing compounds, silicone, and other effective ingredients.

Examples of abrasives include hydrogen calcium phosphate, calcium carbonate, calcium pyrophosphate, insoluble sodium metaphosphate, potassium metaphosphate, silicic acid anhydride, silicic acid hydrate, aluminum silicate, zirconium silicate, bentonite, zeolite, aluminum oxide, aluminum hydroxide, resins and mixtures of these. Among these, silicic acid anhydride, calcium carbonate, zeolite, silicic acid hydrate, and aluminum oxide are especially preferable.

Examples of thickening agents include sodium carboxymethyl cellulose, methyl cellulose, hydroxyethyl cellulose, arginates, carrageenan, gum arabic, polyvinyl alcohol, gum tragacanth, starch, sodium polyacrylate, and the like.

Examples of moisturizers include polyethylene glycol, propylene glycol, sorbitol, glycerine, maltitol, xylitol, and the like. Of these, glycerine, sorbitol, and the like are preferable.

The surfactant is used as a foaming agent or a stabilizing agent for an oil-containing material. Various types of surfactants other than phosphates may be used. Examples of preferable surfactants include sodium alkyl sulfate, sodium alkylbenzenesulfonate, sodium N-acylsarcosinate, N-acylglutamates, polyoxyethylene hydrogenated castor oil, polyoxyethylene-polyoxypropylene block copolymers (pluronic type), fatty acid esters of sucrose, alkylglycosides, fatty acid esters of sorbitan, fatty acid esters of polyoxyethylenesorbitan, alkyldimethylamine oxide, carbobetaine, hydroxycarbobetaine, phosphobetaine, hydroxyphosphobetaine, sulfobetaine, hydroxysulfobetaine, and the like. Of these, water-soluble nonionic and amphoteric surfactants such as polyoxyethylene hydrogenated castor oil, polyoxyethylene-polyoxypropylene block copolymers, fatty acid esters of sucrose, alkylglycosides, fatty acid esters of sorbitan, and fatty acid esters of polyoxyethylenesorbitan, are particular preferable.

Examples of perfumes include natural perfumes such as spearmint oil, peppermint oil, wintergreen oil, sassafras oil, clove oil, sage oil, eucalyptus oil, mayonara oil, cinnamon oil, thyme oil, lemon oil, orange oil, and the like; as well as synthetic perfumes such as l-menthol, anethole, carvone, eugenol, thymol, methyl salicylate, and the like. Examples of sweeteners include saccharin, saccharin sodium, stevioside, neohesperidyldihydrocarcone, berurauchine, p-methoxycinnamic aldehyde, glycyrrhizinates, aspartame (methyl aspartylphenylalanine), and the like. Examples of preservatives include benzoic acid, sodium benzoate, parahydroxybenzoic esters, and the like. Water-soluble fluorine-containing compounds which can be used include sodium fluoride, sodium monofluorophosphate, and the like. Other effective ingredients include chlorophyll compounds, sodium chloride, vitamin C, vitamin E, nicotinic acid esters, allantoinchlorohydroxy aluminum, azulene, lysozyme chloride, hinokitiol, $\beta$-glycyrrhetinic acid, dipotassium glycyrrhizinate, protease, materials extracted from herbal medicines, and the like.

The amounts of these oral vehicles used in the composition of the present invention vary according to the formulation. In the case of a liquid composition, such as mouthrinse, mouthwash, and gargle, any vehicles among the above-mentioned oral vehicles can be incorporated with the exception of the abrasive and the thickening agent. In principle, it is desirable to incorporate 1 to 30% of the moisturizer, and 50 to 96% of alcohol and water. The ratio of alcohol and water is preferably 1:1 to 200:1, and more preferably 5:1 to 100:1. The amount of alcohol in the composition is preferably 1 to 20%.

When the composition is in the form of a paste, such as toothpaste or liquid dentifrice, all of the above-mentioned vehicles can be incorporated. In principle, it is preferable to incorporate 10 to 75% of the abrasive, 0.5 to 5% of the thickening agent, and 10 to 85% of the moisturizer and water. The abrasive is preferably 20 to 75% in the case of a toothpaste, and 10 to 30% in the case of a liquid dentifrice.

For a solid composition such as a toothpowder, the solid ingredients among the above-mentioned vehicles for use in the oral cavity can be blended. Basically, it is preferable to incorporate 60 to 99% of the abrasive.

It is preferable that the total content of the perfume and the sweetener in the oral vehicle be 0.01 to 5%. The pH of the composition of the present invention is in the range of 5 to 9.5, preferably, in the range of 6 to 8.

The component (C) used in the present invention is a surfactant represented by the above general formula (7), wherein $R^{10}$ is a linear or branched alkyl or alkenyl group with 8 to 20 carbon atom is, preferably an alkyl group with 10 to 20 carbon atoms, more preferably 12 to 16 carbon atoms, and most preferably 14 carbon atoms. Specific examples include decyl, lauryl, myristyl, and cetyl groups. $Z^1$ and $Z^2$ are preferably a partial neutralized compound having a neutralization degree of 0.8 to 2.0, especially 1.0 to 1.8. Given as specific examples of component (C) are 1 potassium monodecylphosphate, 1.2 sodium monolaurylphosphate, 1.3 potassium monomyristylphosphate, 1.5 triethanolamine monomyristylphosphate, 1 arginine monomyristylphosphate, 1.3 arginine monomyristylphosphate, 1.2 sodium monocetylphosphate, and the like.

These components (C), when added to a composition containing components (A) and (B), exhibit an action of further extending the period of time for which the composition maintains the antibacterial activity. Although the amount of component (C) to be incorporated into the composition for the oral cavity of the present invention varies depending on the desired antibacterial activity and the types of cation ($A^{m+}$), a preferable amount, in terms of molar ratio, is in the range of $(A^{m+})/(C) = \frac{1}{2}$ to 1/100, with a more preferable amount being in the range of $(A^{m+})/(C) = \frac{1}{2}$ to 1/50. More specifically, in the case of the antibacterial compound of general formula (2), this amount is in the range of $(A^{m+})/(C) = \frac{1}{2}$ to 1/100, and preferably $(A^{m+})/(C) = \frac{1}{2}$ to 1/50; in the case of the antibacterial compound of general formula (3), it is in the range of $(A^{m+})/(C) = \frac{1}{2}$ to 1/20, and preferably $(A^{m+})/(C) = \frac{1}{2}$ to 1/10; and in the case of the antibacterial compound of general formula (4), it is in the range of $(A^{m+})/(C) = \frac{1}{2}$ to 1/50, and preferably $(A^{m+})/(C) = \frac{1}{2}$ to 1/20.

In the present invention, the composition for use in the oral cavity can be prepared either by formulating components (A) and (B) or by formulating component (A'), instead of component (A), and the molar ratio of component (A') to component (C) satisfies $(A')/(C) \leq 1/m$. In the case of the composition in which components (A') and (C) are formulated, it is considered that these components (A') and (C) react in the composition to form a salt.

Given as examples of antibacterial compounds (8) of component (A') are components represented by the following general formulas (9), (10), and (11).

acid residue, and $R^1$, $R^2$, $R^3$, $R^4$, and $R^5$ are the same as defined above.

In the ratio of component (A') to component (C) satisfying the range defined above, an excess amount of component (C) extends the period of time for which the composition maintains the antibacterial activity. In the case where component (C) is added in excess, the molar ratio of $(A^{m+})/(C)$ is preferably $(A^{m+})/(C) = \frac{1}{2}$ to 1/100, and more preferably $(A^{m+})/(C) = \frac{1}{2}$ to 1/50, although it depends on the types of the antibacterial cation ($A^{m+}$). More specifically, in the case of the antibacterial compound of general formula (9), this molar ratio is in the range of $(A^{m+})/(C) = \frac{1}{2}$ to 1/100, and preferably $(A^{m+})/(C) = \frac{1}{2}$ to 1/50; in the case of the antibacterial compound of general formula (10), it is in the range of $(A^{m+})/(C) = \frac{1}{2}$ to 1/20, and preferably $(A^{m+})/(C) = \frac{1}{2}$ to 1/10; and in the case of the antibacterial compound of general formula (11), it is in the range of $(A^{m+})/(C) = \frac{1}{2}$ to 1/50, and preferably $(A^{m+})/(C) = \frac{1}{2}$ to 1/20.

The compounds represented by the general formula (1) used in the present invention can be prepared according to known methods. For example, among compounds of the general formula (1), said compound (2) can easily be prepared from a commercially available quaternary ammonium salt, which is a compound represented by said general formula (9) with a halogen atom as the counter ion, by converting it into the OH-type quaternary ammonium salt, and neutralizing it by said compound having an anion residue. Said compound (3) can be prepared by a method comprising submitting a commercially available compound (10) to alkaline conditions, desalting it by electrodialysis, and neutralizing the product with said compound having an anion residue. An alkali metal salt, an amine salt, an organic amine salt, or a basic amino acid salt may be included during the neutralization to the extent that the neutralization is not hindered.

preferable formulas of the composition for use in the oral cavity of the present invention include liquid formulas such as mouthwash, mouth rinse, and gargle; paste formulas such as toothpaste, liquid dentifrice, and

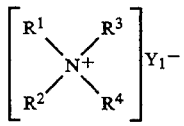

(9)

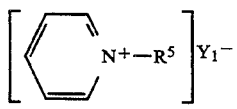

(10)

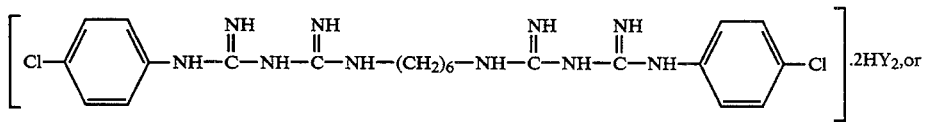

(11)

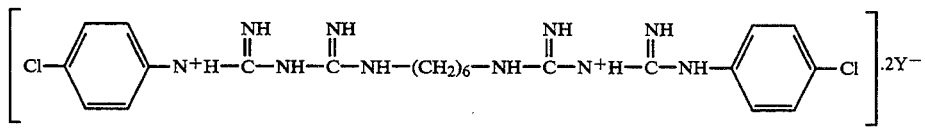

(11')

wherein counter anions $Y^-$ and $Y_1^-$ individually represent a halogen ion, $Y_2$ is a halogen atom or a gluconic gum massage cream; and solid formulas such as toothpowder, and troche.

Among the above compositions for use in the oral cavity of the present invention, a solid composition such as a toothpowder can normally be formulated by mechanically blending the above-mentioned solid ingredients. A composition in the form of a paste can normally be formulated by mechanically blending the various ingredients with deaeration.

In order to disinfect the oral cavity by using the composition for use in the oral cavity of the present invention, the composition is, in principle, preferably applied about 1-3 times per day, about five days a week. Among the forms of the composition, a mouth rinse is the most desirable. Disinfection can be effectively performed using about 10 ml of the mouth rinse of the present invention after brushing, holding in the mouth for about 30 seconds, then ejecting.

The composition for use in the oral cavity of the present invention exhibits a remarkablely rapid disinfection effect and continued antibacterial effect action against oral cavity bacteria while providing a good taste. Its disinfection effect is not reduced in the presence of surfactants. Other features of the invention will become apparent in the course of the following description of the exemplary embodiments which are given for illustration of the invention and are not intended to be limiting thereof.

EXAMPLES

The following compounds were used in the Examples.

Invention Compound 1

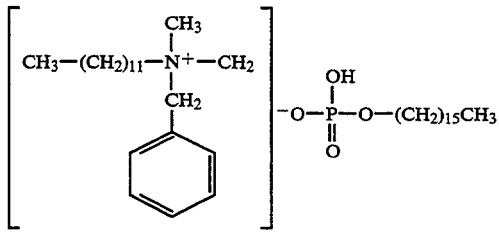

Invention Compound 2

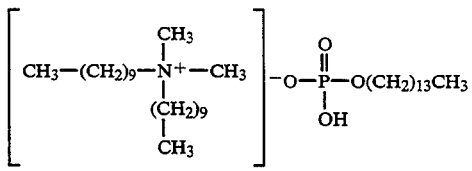

Invention Compound 3

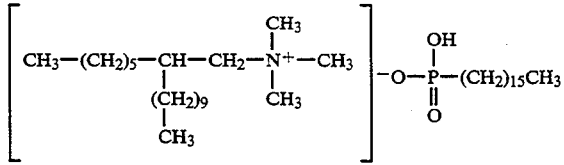

Invention Compound 4

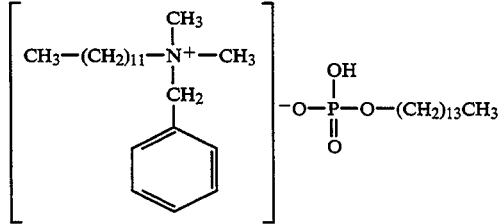

Invention Compound 5

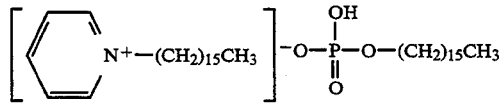

Invention Compound 6

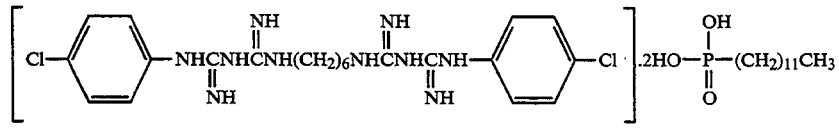

Invention Compound 7

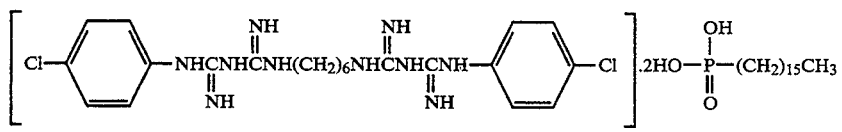

Intervention Compound 8

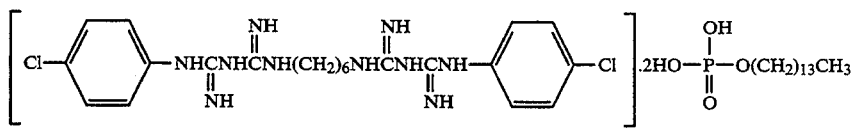

Comparative Compound 1

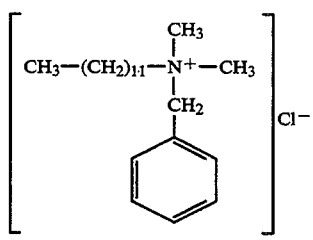

Comparative Compound 2

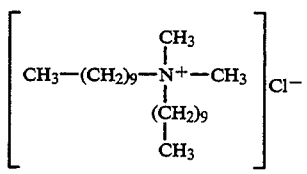

Comparative Compound 3

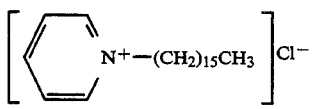

Comparative Compound 4

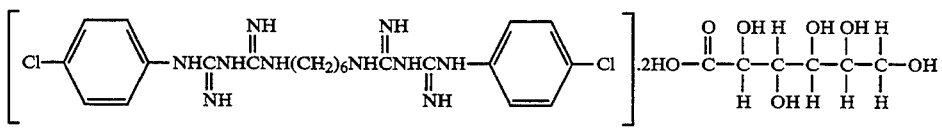

Comparative Compound 5

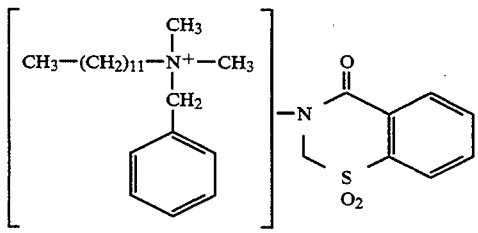

Comparative Compound 6

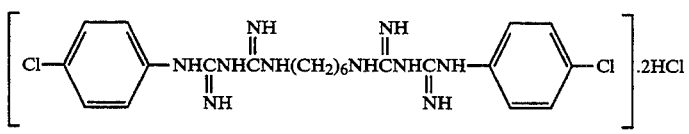

Example 1

Antibacterial compounds in Table 1 were evaluated in terms of their taste.

Evaluation was performed by a panel of 5 adult men and 5 adult women. 20 ml of a 1% ethanol solution containing 0.02% or 0.1% of one of the compounds in Table 1 was held in the mouth for 30 seconds to evaluate the taste while gargling and the aftertaste as one of three grades, O (not bad), D (rather bad), or X (bad). Each compound was graded as one of O, D, or X, to which the average of all panelists is closest. The results are shown in Table 1, which manifestly demonstrates a remarkable improvement in the taste of the composition of the present invention.

the present invention exhibited a remarkably rapid disinfection effect which is not reduced in the presence of surfactants.

TABLE 2

| Composition | Antibacterial compound | Surfactant*1 | Living bacteria (CPU/ml) | | | | |
|---|---|---|---|---|---|---|---|
| | | | Saliva | A. viscosus | C. ochracea | P. gingivalis | S. mutans |
| Blanc | — | — | $1.5 \times 10^7$ | $6.8 \times 10^8$ | $3.8 \times 10^8$ | $4.0 \times 10^8$ | $3.7 \times 10^7$ |
| Invention composition | | | | | | | |
| 1 | Invention Compound 1 | — | $2.0 \times 10^4$ | $2.0 \times 10^6$ | $1.4 \times 10^6$ | $1.5 \times 10^6$ | $1.2 \times 10^5$ |
| 2 | Invention Compound 1 | PHC + MAP | $1.2 \times 10^4$ | $1.3 \times 10^6$ | $1.5 \times 10^6$ | $1.7 \times 10^6$ | $9.2 \times 10^4$ |
| 3 | Invention Compound 1 | CB + MAP | $1.4 \times 10^4$ | $1.1 \times 10^6$ | $9.8 \times 10^5$ | $1.1 \times 10^6$ | $8.8 \times 10^4$ |
| 4 | Invention Compound 2 | — | $8.9 \times 10^3$ | $1.2 \times 10^6$ | $9.2 \times 10^5$ | $8.8 \times 10^5$ | $8.1 \times 10^4$ |
| 5 | Invention Compound 2 | Pluronic F68 + MAP | $7.9 \times 10^3$ | $9.8 \times 10^5$ | $8.9 \times 10^5$ | $7.9 \times 10^5$ | $6.8 \times 10^4$ |
| Comparative composition | | | | | | | |
| 1 | Comparative Compound 3 | — | $3.8 \times 10^4$ | $4.2 \times 10^5$ | $3.3 \times 10^6$ | $2.1 \times 10^6$ | $1.9 \times 10^5$ |
| 2 | Comparative Compound 6 | — | $1.5 \times 10^6$ | $4.5 \times 10^7$ | $2.1 \times 10^7$ | $3.6 \times 10^7$ | $4.1 \times 10^6$ |
| 3 | Triclosan | — | $8.5 \times 10^6$ | $1.1 \times 10^8$ | $8.8 \times 10^7$ | $4.9 \times 10^7$ | $1.3 \times 10^7$ |
| 4 | Triclosan | PHC + MAP | $1.4 \times 10^7$ | $6.2 \times 10^8$ | $3.0 \times 10^8$ | $3.7 \times 10^8$ | $3.2 \times 10^7$ |

TABLE 1

| Antibacterial compound (concentration) | Taste during mouthwash | Taste after mouthwash |
|---|---|---|
| Invention compound | | |
| Compound 1 (0.1%) | O | O |
| Compound 2 (0.1%) | O | O |
| Compound 3 (0.1%) | O | O |
| Compound 4 (0.1%) | O | O |
| Compound 5 (0.02%) | O | O |
| Compound 6 (0.02%) | O | O |
| Compound 7 (0.02%) | O | O |
| Compound 8 (0.02%) | O | O |
| Comparative compound | | |
| Compound 1 (0.1%) | X | X |
| Compound 2 (0.1%) | X | X |
| Compound 3 (0.02%) | D | X |
| Compound 3 (0.1%) | D | X |
| Compound 4 (0.02%) | X | X |
| Compound 4 (0.1%) | X | X |
| Compound 5 (0.1%) | D | D |
| Compound 6 (0.02%) | X | X |

Example 2

A disinfection test was carried out on the compositions shown in Tables 2 and 3.

Bacteria collected from saliva of male adults and bacteria causing diseases in the oral cavity, which are named in Table 2, were used for the test. The antibacterial compounds shown in Tables 2 and 3 were added to the test bacterial suspensions to a concentration of 0.01% in a anaerobic globe box ($N_2:CO_2:H_2 = 80:10:10$, manufactured by Hirasawa Co.), followed by the further addition of surfactants shown in Tables 2 and 3 to a concentration of 0.1%. The mixture was stirred for 1 minute at 37° C., suitably diluted with physiological saline, and cultured for 5 days at 37° C. in BHI agar medium (goat blood hemin and menadione containing, a product of Difco Co.) to measure the number of living bacteria. The results are shogun in Tables 2 and 3, which show that the compositions for the oral cavity of

TABLE 3

| Composition | Antibacterial compound | Surfactant*1 |
|---|---|---|
| Blank Invention composition | — | — |
| 3 | Invention Compound 5 | — |
| 4 | Invention Compound 5 | PHC + MAP |
| 5 | Invention Compound 5 | CB + MAP |
| 6 | Invention Compound 6 | — |
| 7 | Invention Compound 6 | PHC + MAP |
| Comparative composition | | |
| 5 | Comparative Compound 6 | — |
| 6 | Comparative Compound 6 | PHC + SOAP |

*1PHC: Polyoxyethylene (EO = 60) hydrogenated castor oil Emanone CH60, trade mark, manufactured by Kao Corp.)
MAP: Sodium monoalkyl ($C_{12}$) phosphate
CB: Carbo($C_{12}$)betaine (Lauryl dimethylaminoacetic acid betaine; Anhitole 20BS, trade mark, manufactured by Kao Corp.)
Pluronic F68: Polyoxyethylene polyoxypropylene block copolymer (manufactured by Asahi Denka Co.)

Example 3

Benzalkonium chloride (Sanizole, trade mark, a product of Kao Corp.), chlorhexidine gluconate, and cetylpyridinium chloride were selected as antibacterial compounds. An appropriate amount of arginine laurylphosphate (1.3 neutralization) was added to prepare aqueous solutions of antibacterial compound with a concentration of 0.01%. 1 g of hydroxyapatite powder (a product of Wako Pure Chemical Co.), which is a major component of the tooth was added to 20 ml of each solution. After stirring for 30 seconds, the amount the antibacterial compounds in the supernatant was quantitatively measured to calculate their adsorption to the hydroxyapatite.

Figure 2:
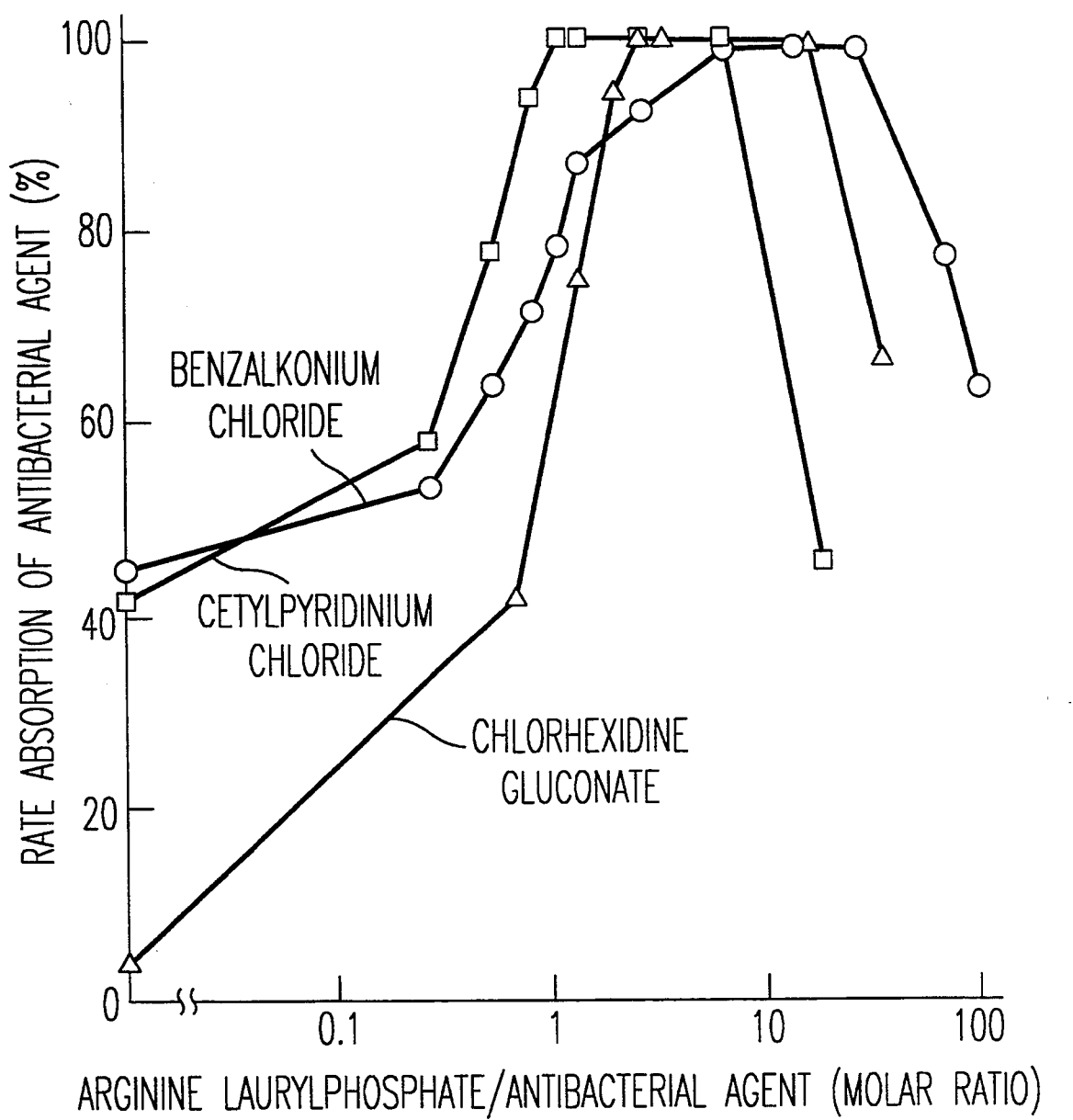
FIG. 2 is a graph showing the rate of adsorption of antibacterial compounds in the compositions according to Example 3.

The results are shown in FIG. 2, which demonstrates that the rate of adsorption is promoted by the addition of arginine laurylphosphate. It was further confirmed that especially good results could be obtained by adjusting the equivalent ratio of benzalkonium chloride and arginine laurylphosphate to 1:1 to 1:100, the molar ratio of chlorhexidine gluconate and arginine laurylphosphate to 1:1 to 50:1, and the equivalent ratio of cetylpyridinium chloride and arginine laurylphosphate to 1:1 to 1:20.

The above results show that the use of the composition for the oral cavity of the present invention can effectively adsorb antibacterial compound to the tooth surface to continuously exhibit the antibacterial action.

Comparative Example 4

Water, 1 mM benzalkonium chloride, 0.5 mM myristylphospholylated di(benzarconium) (1 mM as benzarconium), 1 mM chlorhexidine gluconate, 1 mM cetylpyridinium chloride, 0.5 mM myristylphospholylated di(cetylpyridinium), and 1 mM monomyristylphospholylated chlorhexidine were used as comparative compounds, and 1 mM myristylphospholylated benzalkonium, 1 mM dimyristylphospholylated chlorhexidine, and 1 mM myristylphospholylated cetylpyridinium, to which an appropriate amount of arginine myristylphosphate was added (1.5 neutralization) were used as invention compounds.

Each sample solution was evaluated in terms of the taste during mouthwash and the aftertaste by adult persons by holding 10 ml of the solution in the mouth for 30 seconds while gargling. The rate of bacterial metabolism suppression was determined by collecting saliva after 30 and 60 minutes and measuring its lactic acid producing capability, which is taken as the standard for the antibacterial activity. For the determination of the lactic acid producing capability 0.4 ml of saliva and 0.1 ml of 10% sucrose were reacted for 5 minutes at 37° C., and the reaction product was filtered and submitted to ion chromatography. The rate of suppression of lactic acid production, as the percentage against the amount of lactic acid produced when the person did not wash mouth, was calculated by deducting the amount of lactic acid produced while unreacted as a blank to determine the lactic acid production. The results are shown in Table 4, which indicates that the comparative compounds had unfavorable tastes and hardly maintained their antibacterial effects, while the compounds of the present invention not only provided good taste, but also was proven to promote their prolonged antibacterial effects by the addition of a specific amount of arginine myristylphosphate. Among the above compounds, those having the molar ratio of (antibacterial cation)/(counter anion) greater than the reciprocal of the cation valency, such as myristylphospholylated di(benzalkonium), myristylphospholylated di(cetylpyridinium), and monomyristylphospholylated chlorhexidine, exhibited both unfavorable tastes and poor effects of the continued antibacterial action. On the other hand, the compounds having the molar ratio of (antibacterial cation)/(counter anion) smaller than the reciprocal of the cation valency, such as myristylphospholylated benzarkonium, myristylphospholylated cetylpyridinium, and dimyristylphospholylated chlorhexidine, exhibited both good tastes and excellent effects of the continued antibacterial action.

TABLE 4

| Sample | Taste during mouthwash | After taste | Rate of suppression of lactic acid production After 30 min. | After 60 min. |
|---|---|---|---|---|
| Comparative Example | | | | |
| Water | O | O | −2 | −5 |
| 1 mM benzalkonium chloride | X | X | 4 | 2 |
| 0.5 mM myristylphospholylated di(benzalkonium) | X | X | 6 | 4 |
| 1 mM chlorhexidine gluconate | X | X | 12 | 8 |
| 1 mM cetylpyridinium chloride | X | X | 5 | 2 |
| 0.5 mM myristylphospholylated di(cetylpyridinium) | X | X | 6 | 4 |
| 1 mM monomyristylphospholylated chlorhexidine | X | X | 14 | 10 |
| Examples | | | | |
| 1 mM myristylphospholylated benzalkonium | O | D | 43 | 26 |
| 1 mM myristilphospholylated benzarconium + 2 mM arginine myristylphosphate | O | O | 65 | 48 |
| 1 mM myristilphospholylated benzarconium + 4 mM arginine myristylphosphate | O | O | 52 | 44 |
| 1 mM myristilphospholylated benzarconium + 6 mM arginine myristylphosphate | O | O | 48 | 40 |
| 1 mM myristilphospholylated benzarconium + 8 mM arginine myristylphosphate | O | O | 35 | 31 |
| 1 mM dimyristylphospholylated chlorhexidine | O | O | 42 | 26 |
| 1 mM dimyristylphospholylated chlorhexidine + 2 mM arginine myristylphosphate | O | O | 58 | 51 |
| 1 mM myristylphospholylated cetylpyridinium | O | O | 27 | 21 |
| 1 mM myristylphospholylated cetylpyridinium + 2 mM arginine myristylphosphate | O | O | 37 | 28 |

Example 5

Tooth paste compositions were prepared by blending and deaerating the components shown in Table 5.

TABLE 5

(Unit: %)

| | Composition | | | | | |
|---|---|---|---|---|---|---|
| | 1 | 2 | 3 | 4 | 5 | 6 |
| One of Compounds 1–8 | 0.30 | 0.10 | 0.15 | 0.30 | 0.10 | 0.05 |
| Sodium monoalkyl ($C_{12}$) phosphate | 0.50 | 1.00 | 0.20 | — | — | — |
| Monoalkyl ($C_{12}$) phosphate | — | — | — | 0.80 | 1.00 | 0.20 |
| Sodium hydroxide | — | — | — | 0.18 | 0.22 | 0.04 |
| Polyoxyethylene (EO = 60) hydrogenated castor oil | 0.50 | 1.00 | 2.00 | 0.50 | 1.00 | 2.00 |
| Triethanolamine | — | — | — | — | — | 0.10 |
| Aluminum hydroxide | 35.00 | 35.00 | 35.00 | 35.00 | 35.00 | 35.00 |
| Silicic acid anhydride | 5.00 | 5.00 | 5.00 | 5.00 | 5.00 | 5.00 |
| Hydroxyethyl cellulose | 0.40 | 0.40 | 0.40 | 0.40 | 0.40 | 0.40 |
| Sodium lauryl sulfate | 0.20 | — | — | 0.20 | — | — |

TABLE 5-continued

| | Composition (Unit: %) | | | | | |
|---|---|---|---|---|---|---|
| | 1 | 2 | 3 | 4 | 5 | 6 |
| Saccharin sodium | 0.10 | 0.15 | 0.15 | 0.10 | 0.15 | 0.15 |
| Glycerine | 10.00 | 10.00 | 10.00 | 10.00 | 10.00 | 10.00 |
| 70% sorbit solution | 15.00 | 20.00 | 20.00 | 15.00 | 20.00 | 20.00 |
| Perfume | 0.80 | 0.90 | 0.90 | 0.80 | 0.90 | 0.90 |
| Purified water | q.s. | q.s. | q.s. | q.s. | q.s. | q.s. |
| Total | 100.00 | 100.00 | 100.00 | 100.00 | 100.00 | 100.00 |

Example 6

Concentrated mouthwash compositions 7 and 8 were prepared by blending the components shown in Table 6. The composition can be used after diluting to a volume of about 30 fold.

TABLE 6

| | Composition (Unit: %) | |
|---|---|---|
| | 7 | 8 |
| Invention Compound 2 | 15.00 | — |
| Invention Compound 8 | — | 15.00 |
| 1 Sodium myristylphosphate | 15.00 | — |
| 1.2 Sodium myristylphosphate | — | 15.00 |
| Ethanol | 20.00 | 20.00 |
| Saccharin sodium | 1.00 | 1.00 |
| Dipotassium glycyrrhizinates | 0.50 | 0.50 |
| Polyoxyethylene (EO = 40) hydrogenated castor oil | 3.00 | 3.00 |
| Perfume | 3.00 | 3.00 |
| Colorant | Slight amount | Slight amount |
| Purified water | q.s. | q.s. |
| Total | 100.00 | 100.00 | were prepared by blending the components shown in Table 7 and molding the blend into a disk shape by a tabletting machine.

TABLE 7

| | Composition (Unit: %) | |
|---|---|---|
| | 9 | 10 |
| Invention Compound 4 | 0.10 | — |
| Invention Compound 5 | — | 0.10 |
| Citric acid | 0.20 | 0.20 |
| Aspartame | 0.10 | 0.10 |
| Lysozyme chloride | 0.50 | 0.50 |
| Gum arabic | 5.00 | 5.00 |
| Perfume | Slight amount | Slight amount |
| Lactose | q.s. | q.s. |
| Total | 100.00 | 100.00 |

Example 8

An aqueous solution of benzethonium chloride or cetylpyridinium chloride and an aqueous solution of sodium monoalkyl ($C_{12}$) phosphate (pH 7) were mixed to produce white precipitate. To the mixture were added ethanol and polyoxyethylene (EO=40) hydrogenated castor oil to solubilize the precipitate. Mouthwash compositions 11 and 12 were prepared by adding other components shown in Table 1 and blending the mixture.

TABLE 8

| | Composition (Unit: %) | |
|---|---|---|
| | 11 | 12 |
| Benzethonium chloride | 0.10 | — |
| Cetylpyridinium chloride | — | 0.10 |
| Sodium monoalkyl ($C_{12}$) phosphate | 0.20 | 0.20 |
| Ethanol | 10.00 | 10.00 |
| Saccharin sodium | 0.10 | 0.10 |
| Polyoxyethylene (EO = 40) hydrogenated castor oil | 1.00 | 1.00 |
| Perfume | 0.30 | 0.30 |
| Colorant | Slight amount | Slight amount |
| Purified water | q.s. | q.s. |
| Total | 100.00 | 100.00 |

Example 9 (Mouthwash)

The following oil components and water components were dissolved separately and two solutions were mixed to obtain a transparent mouthwash composition. Preferable use of this composition is holding it in mouth after blushing teeth for about 30 seconds and then ejecting.

| (Oil components) | |
|---|---|
| Monoalkyl phosphate ($C_{14}$) | 0.25% |
| Polyoxyethylene (EO = 20) sorbitan monostearate | 0.10 |
| Methyl p-hydroxybenzoate | 0.05 |
| Ethanol | 4.00 |
| Perfume | 0.12 |
| (Water components) | |
| L-Arginine | 0.23 |
| Sorbit solution (70%) | 8.00 |
| Glycerine | 8.00 |
| Saccharin sodium | 0.01 |
| Benzalkonium chloride | 0.05 |
| Purified water | Balance |
| Total | 100.0% |

Obviously, numerous modifications and variations of the present invention are possible in light of the above teachings. It is therefore to be understood that within the scope of the appended claims, the invention may be practiced otherwise than as specifically described herein.

What is claimed is:

1. A composition for use in the oral cavity comprising:

(A) an antibacterial compound represented by the following general formula (1), $$A^{m+} \cdot X_m^{-} \quad (1)$$

wherein $A^{m+}$ is a nitrogen-containing antibacterial cation and the counter anion $X^{-}$ represents a monoalkyl phosphate ion, a monoalkenyl phosphate ion, a monoalkyl phosphonate ion, or a monoalkenyl phosphonate ion having a linear or branched alkyl or alkenyl group with 8 to 20 carbon atoms, and m is a valence of the cation A, and (B) a vehicle for use in the oral cavity;
wherein said antibacterial compound (A) is selected from the group consisting of:
a compound represented by the following formula (2),

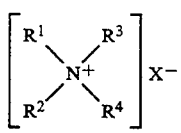 (2)

wherein at least one of $R^1$, $R^2$, or $R^3$ is a linear or branched alkyl or alkenyl group with 8 to 30 carbon atoms, and others are individually a group selected from methyl group, ethyl group, benzyl group, and a group represented by one of the following formulas,

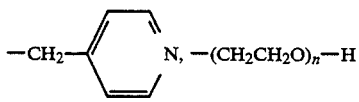

(wherein n is an integer of 1 to 15),

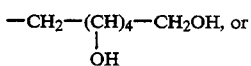

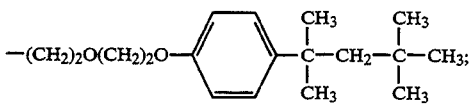

$R^4$ represents a group —$CH_3$, —$CH_2CH_3$, or —$CH_2CH_2OH$; and the counter anion $X^-$ is defined above;

a compound represented by the following formula (3),

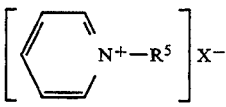 (3)

wherein $R^5$ is a linear or branched alkyl group with 10 to 20 carbon atoms and $X^-$ is defined above; and a compound represented by the following formula (4),

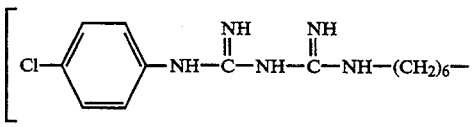

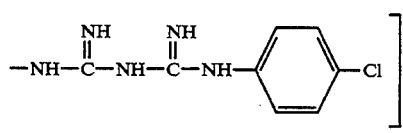 .2HX   (4)

wherein each X may be the same or different and each individually represents a monoalkyl phosphate group, a monoalkenyl phosphate group, a monoalkyl phosphonate group, or a monoalkenyl phosphonate group having a linear or branched alkyl or alkenyl group with 8 to 20 carbon atoms.

2. A composition for use in the oral cavity according to claim 1, wherein said counter anion $X^-$ is a phosphate ion represented by the following general formula (5),

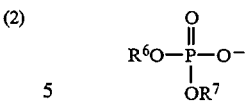 (5)

wherein $R^6$ is a linear or branched alkyl or alkenyl group with 8 to 20 carbon atoms and $R^7$ is a hydrogen atom, an alkali metal, an alkyl ammonium group, an alkyl ammonium group with a substituted hydroxy group, or a basic amino acid group, said basic amino acid being arginine.

3. A composition for use in the oral cavity according to claim 1, wherein said counter anion $X^-$ is a phosphonate ion represented by the following general formula (6),

 (6)

wherein $R^8$ is a linear or branched alkyl or alkenyl group with 8 to 20 carbon atoms and $R^9$ is a hydrogen atom, an alkali metal, an alkyl ammonium group, an alkyl ammonium group with a substituted hydroxy group, or a basic amino acid group, said basic amino acid being arginine.

4. A composition for use in the oral cavity according to claim 1, further comprising, (C) a surfactant represented by the following general formula (7),

 (7)

wherein $R^{10}$ is a linear or branched alkyl or alkenyl group with 8 to 30 carbon atoms, and $Z^1$ and $Z^2$ may be the same or different and each individually represents a hydrogen atom, an alkali metal, an alkyl ammonium group, an alkyl ammonium group with a substituted hydroxy group, or a basic amino acid group, said basic amino acid being arginine.

5. A composition for use in the oral cavity comprising:

(A') an antibacterial compound represented by the following general formula (8),

 (8)

wherein $A^{m+}$ is a nitrogen-containing antibacterial cation and the counter anion $Y^-$ represents a halogen ion or a gluconate ion, and m is a valence of the cation A, (B) a vehicle for use in the oral cavity, and (C) a surfactant represented by the following general formula (7),

 (7)

wherein $R^{10}$ is a linear or branched alkyl or alkenyl group with 8 to 30 carbon atoms, and $Z^1$ and $Z^2$ may be the same or different and each individually represents a hydrogen atom, an alkali metal, an alkyl ammonium group, an alkyl ammonium group with a substituted hydroxy group, or a basic amino acid group, said basic amino acid being arginine; and wherein the molar amount of component (C) is m times or more of that of component (A');

wherein said antibacterial compound (A') is selected from the group consisting of:

a compound represented by the following formula (9),

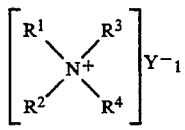
(9)

wherein at least one of $R^1$, $R^2$, or $R^3$ is a linear or branched alkyl or alkenyl group with 8 to 30 carbon atoms, and others are individually a group selected from methyl group, ethyl group, benzyl group, and a group represented by one of the following formulas,

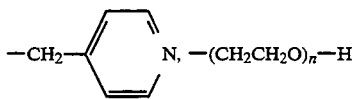

(wherein n is an integer of 1 to 15),

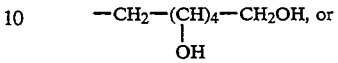

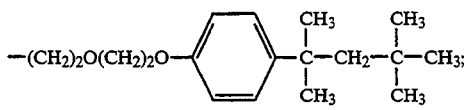

$R^4$ represents a group —$CH_3$, —$CH_2CH_3$, or —$CH_2CH_2OH$; and the counter anion $Y_1^-$ represents a halogen ion;

a compound represented by the following formula (10);

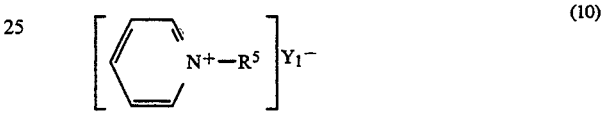
(10)

wherein $R^5$ is a linear or branched alkyl group with 10 to 20 carbon atoms and $Y^-$ is a halide ion, and a compound represented by the following formula (11),

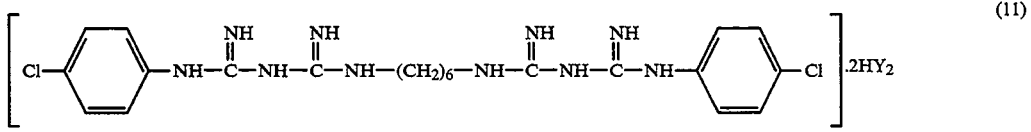
(11)

wherein $Y_2$ represents a halogen atom or a gluconate ion, wherein (A') and (C) react to form a salt.

* * * * *